United States Patent [19]

Hill et al.

[11] Patent Number: 4,820,636
[45] Date of Patent: Apr. 11, 1989

[54] ELECTROCHEMICAL ASSAY FOR CIS-DIOLS

[75] Inventors: Hugh A. O. Hill, Oxford; Monika J. Green, Leckhampstead, both of Great Britain

[73] Assignee: Medisense, Inc., Cambridge, Mass.

[21] Appl. No.: 832,452

[22] Filed: Feb. 21, 1986

[30] Foreign Application Priority Data

Feb. 21, 1985 [GB] United Kingdom ............... 8504521

[51] Int. Cl.[4] .................. C12Q 1/54; C12Q 1/48; G01N 33/72; C07F 9/02
[52] U.S. Cl. .................................. 435/14; 435/4; 435/15; 435/817; 435/25; 436/67; 260/502.3; 556/7
[58] Field of Search .............. 435/4, 14, 15, 817, 435/180; 436/67; 260/502.3; 556/7

[56] References Cited

U.S. PATENT DOCUMENTS 4,205,952  6/1980  Cais ..................... 436/518
4,409,335 10/1983  Hanamoto et al. ............ 436/67
4,545,382 10/1985  Higgins et al. .............. 435/180
4,582,806  4/1986  Bowsher et al. .............. 435/15
4,659,817  4/1987  Gallop et al. ............... 556/7

OTHER PUBLICATIONS

Middle et al., "Separation of Glycosylated Hemoglobins Using Immobilized Phenylboronic Acid," Chem. Abst. 99:172205f, 1983.
"Affi-Gel 601", catalog.
"GlyoTest Kits", Pierce Chemical Company, Rockford, Ill.
"Glyco Gel", Pierce Chemical Company, Rockford, Ill.

Primary Examiner—Sam Rosen
Assistant Examiner—Janelle Graeter

[57] ABSTRACT

The invention disclosed relates to an electrochemical assay which is particularly concerned with an assay for the presence of, or amount of, glycosylated haemoglobin in a blood sample, but which extends to a general assay for detecting the presence of, monitoring the level of or determining the concentration of compounds containing cis-diol groups, such as glycols, nucleic acid components, sugars, polyols, catechols and glycosylated proteins.

When ferrocene boronic acid or a derivative thereof is present free in solution, it can act as a mediator for a wide range of oxido-reductases. However in the presence of, for example, sugars containing the cis-diol structure, the metallocene (such as ferrocene boronic acid) covalently binds to the sugar. When the ferrocene boronic acid is thus bound, it is essentially immobilized and its properties as a mediator and ability to diffuse will be markedly affected.

6 Claims, 2 Drawing Sheets

I

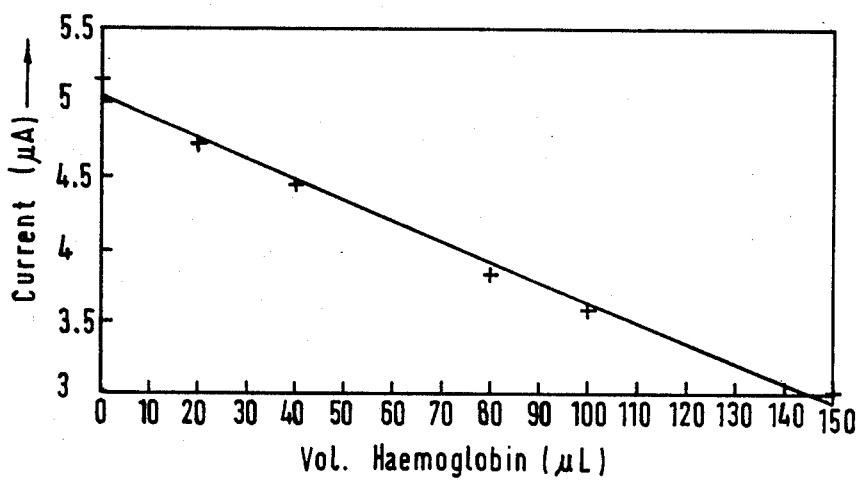
FIG.4.
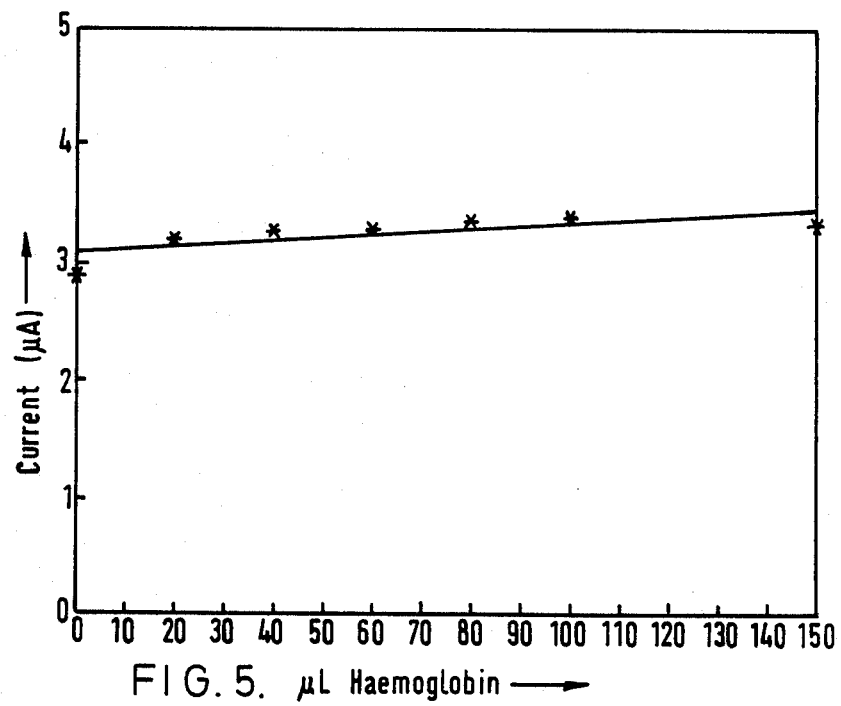
FIG.5. μL Haemoglobin ⟶

ELECTROCHEMICAL ASSAY FOR CIS-DIOLS

FIELD OF INVENTION

The present invention relates to an electrochemical assay which is particularly concerned with an assay for the presence of, or amount of, glycosylated haemoglobin in a blood sample, but which extends to a general assay for detecting the presence of, monitoring the level of or determining the concentration of compounds containing cis-diol groups, such as glycols, nucleic acid components, sugars, polyols, catechols and glycosylated proteins. While use may be made of this invention to the chemical industry, especially where complex mixtures are encountered (e.g. in food chemistry or biochemical engineering), it is of particular value in biological investigation and control techniques.

For convenience, the invention will be described, inter alia, with reference to the determination of glucose management in a diabetic human subject by the use of equipment usable on a specific or occasional basis. While the provision for sensors of components in biological fluids is one object of the invention, other and broader objects are not hereby excluded.

PRIOR ART

The glycosylated adducts of haemoglobin mentioned above form a series of compounds after reaction between haemoglobin A and sugar or sugar-phosphates. This class of compounds is also known as the "fast" haemoglobins and was first recognised by the rapid migration exhibited during electrophoresis on cation-exchange chromatography. The adducts $HbA_{1a}$, $HbA_{1b}$ and $HbA_{1c}$ have been separated by such chromatographic methods.

Measurement of glycosylated haemoglobin has become a common technique for the identification of diabetes and and important therapeutic index for long-term blood glucose control in diabetes mellitus. The most common glycosylated haemoglobin ($HbA_{1c}$) is formed, both in normals and diabetics, by the non-enzymatic attachment of glucose to the N-terminal valine of one or both of the haemoglobin-A beta-chains to form a stable ketoamine. The reaction occurs at a rate which is dependent on the blood glucose concentration. The level of glycosylation therefore reflects the mean concentration of blood glucose over the lifetime of the red blood cells (approx. 120 days) and can therefore provide a measure of extended metabolic control. It is known that the level of glycosylation can double or treble in diabetic patients.

In non-diabetics the level of $HbA_{1c}$ is about 5-6% of the total haemoglobin. In a diabetic patient this level is normally slightly higher (8-9%), when particular care is being taken to control the glucose level. If the $HbA_{1c}$ level rises above 12-13%, there is a strong indication that the level of blood glucose is not being adequately maintained below the permissible upper limit, and the patient will begin to suffer from the effects of a high blood sugar level.

An early assay technique for the glycosylated haemoglobins was the Trivelli macrocolumn technique [Trevelli, Ranney and Lai, New England Journal of Medicine 284, 353-357, 1971]. This technique was followed by the development of improved chromatographic methods by Goldstein et al. [Diabetes, Vol. 31, Supplement 3, June 1982].

Recent studies have indicated that other sugar-adducts of haemoglobins exist, such as those formed between glucose and the epsilon amino group of lysine residues in haemoglobin A. Furthermore abnormal haemoglobins (such as 'Wayne' haemoglobin) will often separate out with the glucose adducts during electrophoresis and/or chromatography. In at least one case Wayne haemoglobin has been mistaken for glycosylated haemoglobin, during chromatographic analysis.

At present none of the available methods for the assay of glycosylated haemoglobins are accurate enough to give a good quantization of the degree of sugar-adduct formation, and there is no established reference method. In the Goldstein method, control glycosylated haemolysates must be held at $-70$ degrees Celsius when not in use, as the level of glycosylation slowly increases at higher temperatures. All other known methods are cumbersome to perform and time-consuming. None of the methods can been seen as the basis for a home diagnostics kit

DESCRIPTION OF THE INVENTION

According to a first aspect of the present invention there is provided an assay for cis-diols in a sample, which assay comprises;

(a) treating the sample with a known excess of metallocene boronic acid or a derivative thereof, whereby the metallocene boronic acid will bind to any cis-diol groups present, and, (b) determining the quantity of free metallocene boronic acid in the mixture. Conveniently, the quantity of free metallocene boronic acid is determined by its activity as a mediator, that is, a charge transferring compound which enables the course of an enzyme catalysed reaction to be detected, measured or monitored.

When a metallocene boronic acid, such as a ferrocene boronic acid, is present free in solution, it can act as a mediator for a wide range of oxido-reductases. However in the presence of, for example, sugars containng the cis-diol structure, the metallocene boronic acid covalently binds to the sugar. When the metallocene is thus bound, it is essentially immobilized and its properties as a mediator and ability to diffuse will be markedly affected.

European Patent Application No. 82305597 and U.S. Pat. No. 4,545,382, which is hereby incorporated by reference, describe and claim a sensor electrode composed of electrically conductive material and comprising at least at an external surface thereof the combination of an enzyme and a mediator compound which transfers electrons to the electrode when the enzyme is catalytically active. The purpose of such an electrode is to detect the presence of, measure the amount of and/or monitor the level of one or more selected components capable of undertaking a reaction catalysed by the said enzyme. Examples of electrode configurations, mediators and uses are given in that and later patent applications.

This specification makes use of the chemical properties of the mediators and their derivatives to detect the presence of a chemical species (the cis-diol configuration) with which the boronic acid derivatives can form a covalent linkage.

Preferably the metallocene is ferrocene or a derivative thereof of known concentration.

According to a second aspect of the present invention there is provided a reagent for use in the assay of cis-diols, the said reagent comprising the compound;

X—B(OH)$_2$ where X is a metallocene.

Conveniently, X is ferrocene or a derivative thereof, preferably, aminophenyl ferrocene.

Ferrocenes (bis-cyclopentadienyl iron and its derivatives) have advantages over other mediators used with enzyme/substrate reactions for charge-transfer purposes. Ferrocenes have:

(a) a wide range of redox potentials accessible through substitution of the cyclopentadienyl rings which can be functionalised;

(b) electrochemically reversible one-electron redox properties;

(c) a pH-independent redox potential and a slow autoxidation of the reduced form.

According to a third aspect of the present invention there is provided an assay for glycosylated haemoglobin in a sample, which includes the steps of;

(a) treating the sample with a known excess of metallocene boronic acid or a derivative thereof, and, (b) determining the quantity of free metallocene boronic acid remaining in the assay mixture.

Typically the quantity of free metallocene boronic acid in the assay mixture is determined by the addition to the assay mixture of a known quantity of a redox enzyme, in the presence of a substrate for that enzyme, and the measurement of charge transfer to an electrode surface in contact with the assay mixture.

Preferably the sample is a blood sample.

According to a fourth aspect of the present invention there is provided a reagent for use in a method of assay comprising a solution of 3-aminophenyl ferrocene boronic acid i.e. the following compound;

Cp.Fe.Cp—CO—NH—C$_6$H$_4$—B(OH)$_2$ known as 3-aminophenyl ferrocene boronic acid.

Although the present invention has so far been described with respect to the assay of diabetic blood, it should be noted that the invention is not intended to be limited to this field and can be applied to the assay of other cis-diol containing analytes: glycoproteins, plasma proteins, enzymes, (e.g. amylase, catalase, hexokinase, serine proteases), nucleotidyl peptides, glycolipids, ATP, nucleic acid components, glycols, sugars, polyols and catechols can be assayed.

BRIEF DESCRIPTION OF THE DRAWINGS

In order that the invention may be better understood it will be described by way of example and with reference to the accompanying drawings wherein;

Turning to FIG. 1, there is shown a general reaction scheme for the addition of the tautomeric form of boronic acid to the cis-diol, to form the product with the elimination of water.

EXAMPLE 1

Preparation of 3 Ferrocene Aminophenyl Boronic Acid

Figure 1:
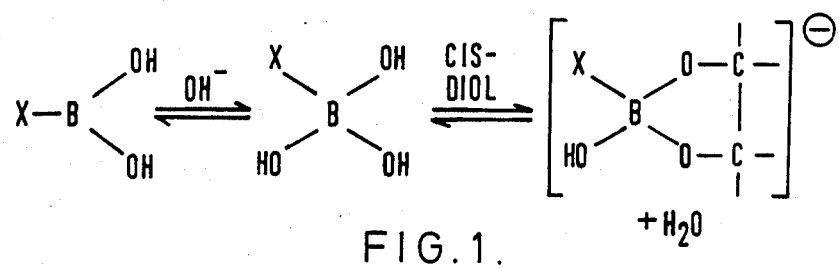
FIG. 1; shows the nature of the reaction between boronic acid and cis-diols.
Figure 2:
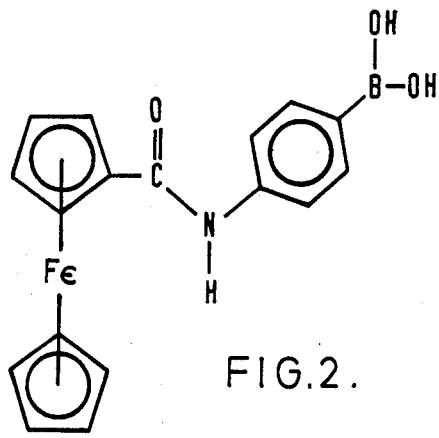
FIG. 2; shows 3-aminophenyl ferrocene boronic acid.

FIG. 2 illustrates the preferred metallocene to be used with the present invention. The compound (I) is 3 ferrocene aminophenyl boronic acid (bis-cyclopentadienyl iron monocarboxyamide N-phenyl boronic acid), as anilide derivative of ferrocene monocarboxylic acid.

In order to prepare (I) 3-aminophenyl boronic hemisulphate was dissolved in water by adjusting to pH 7.2 with sodium hydroxide solution. The water was removed and the residue dissolved in dioxane. The dioxane was then removed.

The residue was stirred in the dark with 7.0 g.dicyclo hexylcarbodiimide, 10 mg dimethyl aminopyridine and 3.2 g ferrocene monocarboxylic acid in 30 ml of diemethyl formamide (DMF) for 24 hrs.

The resulting solution was filtered and the DMF removed. Hexane (300 ml) was added to the solid and oil remaining in the flask and the mixture stirred for 70 hrs. The hexane was decanted and the solid washed with three portions of diethyl ether, then dissolved in a minimum volume of ethanol for chromatographic separation of the product on a fluorisil column packed in 3 parts diethyl ether to 2 parts hexane. Initial elution with this mixture eluted one ferrocene-combining component, a second component was eluted with ethanol.

Analysis of the second component by HPLC showed only one peak, and it was determined that the mass-spectroscopy results were consistent with the product being 3-ferrocene aminophenylboronic acid. (I).

EXAMPLE 2

Calibration Curve for Glycosylated Haemoglobin

Figure 3:
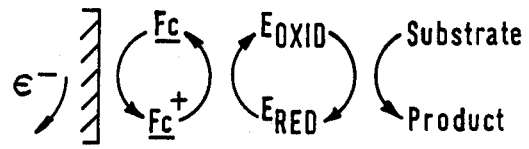
FIG. 3; shows a general schematic for the mediation between an enzyme and an electrode using ferrocene, FIG. 4; shows a calibration curve of current against added volume of glycosylated haemoglobin for an assay system according to the present invention, FIG. 5; shows the results of a control experiment in which ferrocene carboxylic acid was employed.

FIG. 3 illustrates a general reaction showing the mediation between an enzyme and an electrode using ferrocene. The ferrocene (Fc+) picks up electrons from the reduced form of the enzyme (E$_{red}$) and is reduced itself in the process. The reduced ferrocene (Fc) is oxidised at the electrode to regenerate the oxidixed form. The reduced form of the enzyme is regenerated by the oxidation of the substrate. Thus both the enzyme and the ferrocene perform catalytic roles in the reaction, and any change in the availability of either of these two species will affect the rate of transfer of charge to the electrode. In the present invention, the availability of the ferrocene is changed by the effective removal of free ferrocene from the system either in part or in total. This is accompanied by the reaction with the cis-diol structure when such a structure is present in the assay mixture.

In order to demonstrate the effectiveness of the present technique, human haemoglobin (Sigma, Lot 95F-9330) was prepared to a concentration of 2.5 g/dl in Tris-HCl buffer (20 mM, pH 8.0). The percentage of haemoglobin in the glycosylated form was determined at 9.66% using a Bio-Rad (Trademark) haemoglobin A$_1$ cation-exchange assay.

Various volumes of this solution (0–150 μl) were added to a mixture comprising 3-aminophenyl ferrocene boronic acid ($10^{-5}$M) in the same buffer (500 μl) and incubated at room temperature for one minute.

Glucose oxidase (40 Units) was added and a cyclic voltammogram scanned over the range +250-650 mV vs. SCE. After correction for dilution factors, a calibration curve of current against glycosylated protein was produced. Such a plot is shown in FIG. 4.

FIG. 5 shows the results of a control experiment with ferrocene monocarboxylic acid.

Although the present invention has been described by example in terms of a strip electrode for the assay of glycosylated haemoglobin, it should be understood that the present invention extends to a general assay for the presence of cis-diol structures as outlined above. The invention further extends to;

(a) metallocene boronic acid derivatives for use in either a wet or dry assay according to the present invention, and, (b) electrodes, cells and assay apparatus comprising metallocene boronic acid derivatives, for use in the assay of chemical species containing the cis-diol structure according to the present invention.

We claim:

1. A method of electrochemical assay for cis-diol in a sample, which assay includes the steps of:
    (a) providing a measured amount of metallocene boronic acid compound which is an electroactive mediator capable of mediating an enzyme-catalyzed reation and which is able to bind the cis-diol to modify the mediating capability of said metallocene boronic acid compound;
    (b) treating the sample with a known excess of said metallocene boronic acid compound to bind to any cis-diol in said sample and to leave unbound some of said metallocene boronic acid compound;
    (c) providing substrate and enzyme for said enzyme-catalysed reaction;
    (d) electrochemically determining unbound metallocene boronic acid compound by admixing said treated sample with said substrate and said enzyme, and monitoring electrical charge passed by said unbound metallocene boronic acid compound acting as a mediator; and
    (e) determining said cis-diol by derivation from said determination of said unbound metallocene boronic acid compound.

2. An assay as claimed in claim 1 wherein, the metallocene is ferrocene or a derivative thereof functional in the assay.

3. An assay as claimed in claim 2 wherein, the metallocene is 3-aminophenyl ferrocene.

4. A method of electrochemical assay for glycosylated hemoglobin in a sample, which assay includes the steps of:
    (a) providing a measured amount of metallocene boronic acid compound which is an electroactive mediator capable of mediating an enzyme-catalyzed reaction and which is able to bind the glycosylated hemoglobin to modify the mediating capability of said metallocene boronic acid compound;
    (b) treating the sample with a known excess of said metallocene boronic acid compound to bind to any glycosylated hemoglobin in said sample and to leave unbound some of said metallocene boronic acid compound;
    (c) providing substrate and enzyme for said enzyme-catalysed reaction;
    (d) electrochemically determining unbound metallocene boronic acid compound by admixing said treated sample with said substrate and said enzyme, and monitoring electrical charge passed by said unbound metallocene boronic acid compound acting as a mediator; and
    (e) determining said glycosylated hemoglobin by derivation from said determination of said unbound metallocene boronic acid compound.

5. An assay as claimed in claim 4, wherein the sample is a blood sample.

6. An assay as claimed in claim 5 wherein the quantity of free metallocene boronic acid in the assay mixture is determined by the addition to the assay mixture of a known quantity of a redox enzyme, in the presence of a substrate for that enzyme, and the measurement of charge transfer to an electrode surface in contact with the assay mixture.

* * * * *